United States Patent [19]

Hall

[11] Patent Number: 5,084,250

[45] Date of Patent: Jan. 28, 1992

[54] APPARATUS FOR TREATING AND DISPOSING OF BIO-HAZARDOUS WASTE AND SOLID WASTE

[75] Inventor: John Hall, Tracy, Calif.

[73] Assignee: Bromac Enterprises, a partnership, Tracy, Calif.

[21] Appl. No.: 471,394

[22] Filed: Jan. 29, 1990

[51] Int. Cl.⁵ .............................................. A61L 2/00
[52] U.S. Cl. ................................... 422/292; 422/26; 422/295; 422/299; 422/300; 100/73
[58] Field of Search ............... 422/26, 292, 295, 299, 422/300, 291; 100/70 R, 71, 73-75

[56] References Cited

U.S. PATENT DOCUMENTS

| | | | |
|---|---|---|---|
| 3,088,179 | 5/1963 | Leuthner | 422/295 |
| 4,166,096 | 8/1979 | Gillis et al. | 422/299 |
| 4,374,491 | 2/1983 | Stortroen et al. | 422/26 |
| 4,552,720 | 11/1985 | Baker, Sr. et al. | 422/26 |

Primary Examiner—David L. Lacey
Assistant Examiner—William H. Beisner
Attorney, Agent, or Firm—Harris Zimmerman

[57] ABSTRACT

Apparatus for storing and processing waste materials at hospitals or the like includes a housing having an access opening in a sidewall for receiving wastes and a discharge opening at the base of an end wall. Non-hazardous wastes are stored in a compartment adjacent the discharge opening. A compactor ram is periodically traveled across the compartment and into the discharge opening to transfer wastes to an adjacent receiver of the type that can be transported to a disposal site. Infectious wastes are stored in a separate sealable receptacle from which air is periodically evacuated and replaced with steam to sterilize the contents. Motors then swivel the receptacle away from the housing access passage and tilt the receptacle to dump the sterilized contents into the non-hazardous storage compartment.

12 Claims, 3 Drawing Sheets

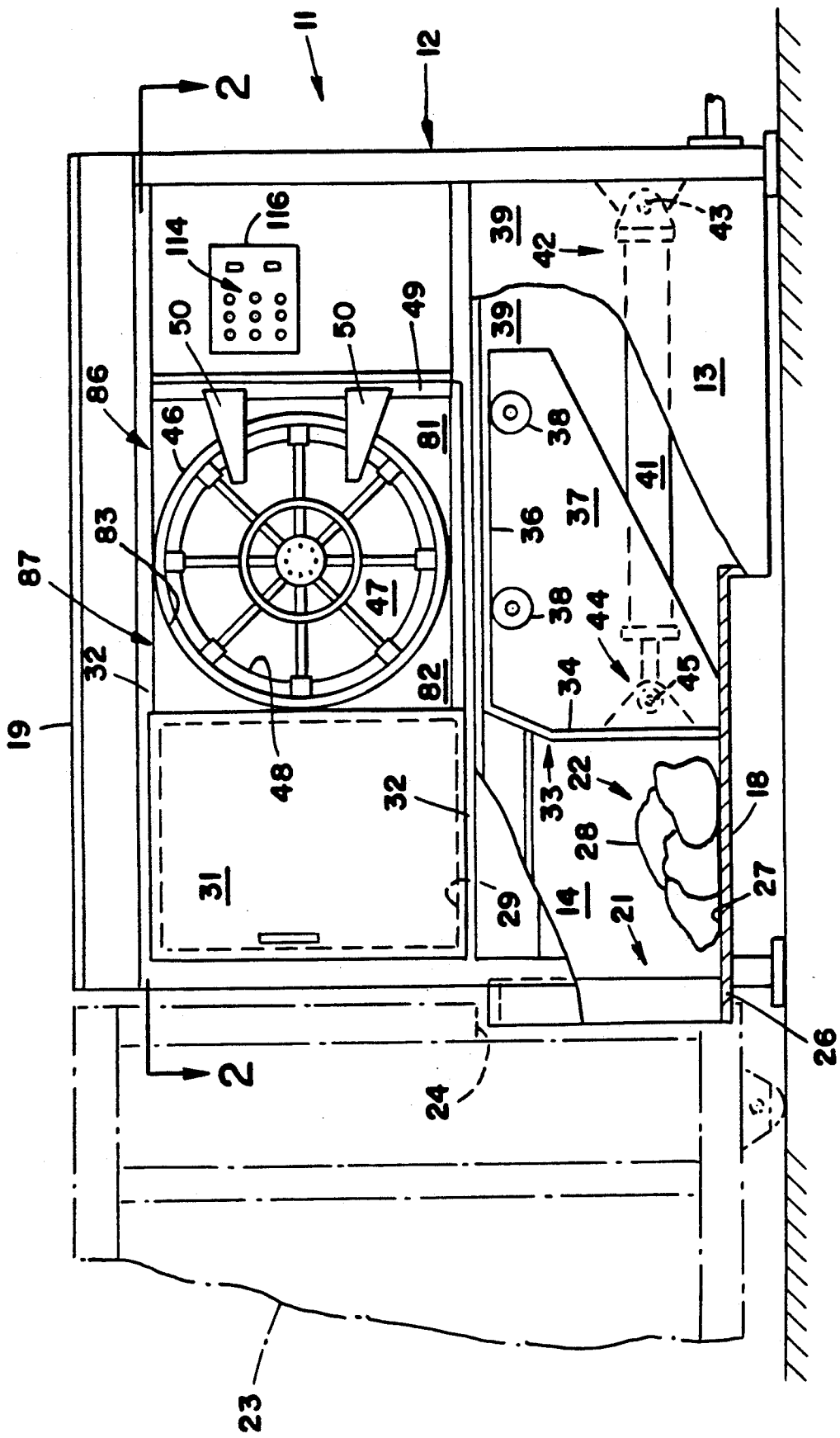
FIG_1

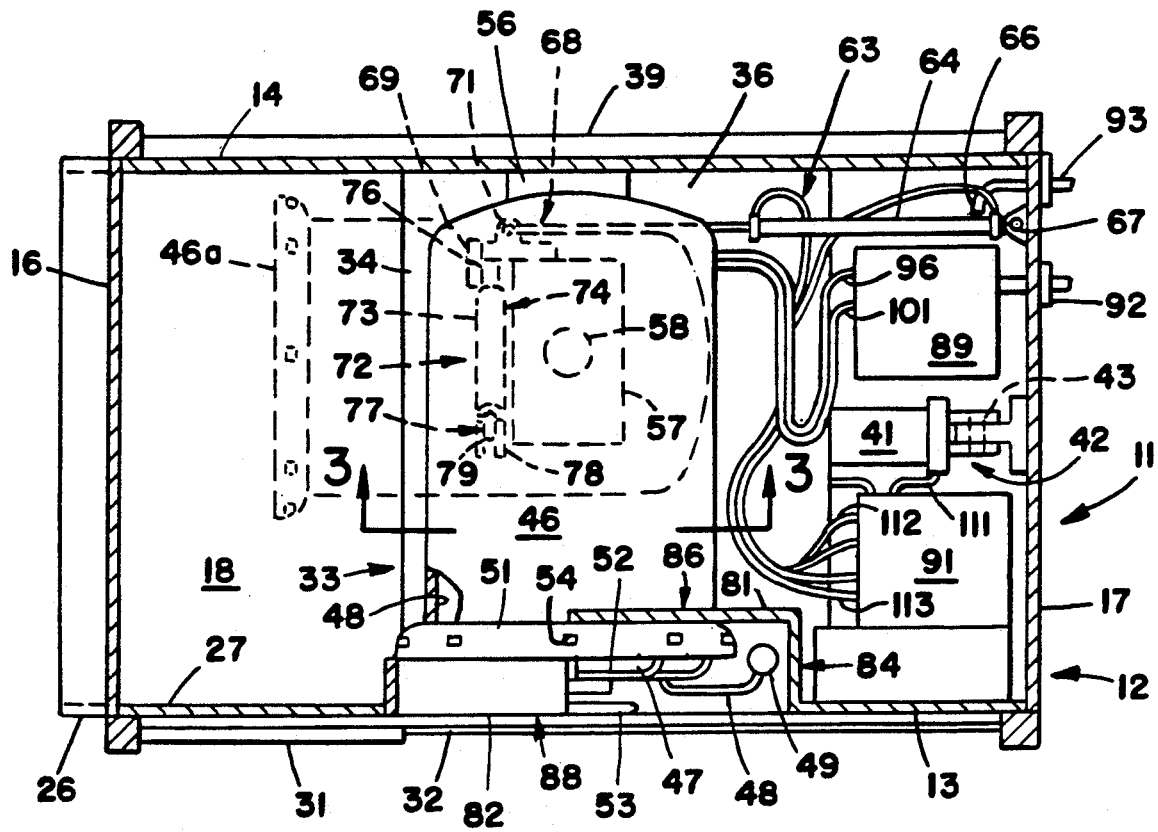
FIG_2
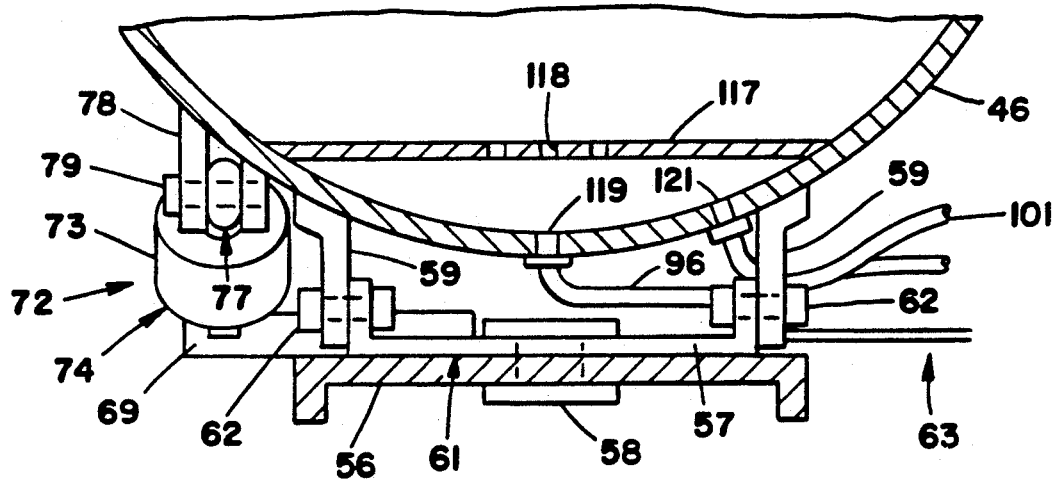
FIG_3

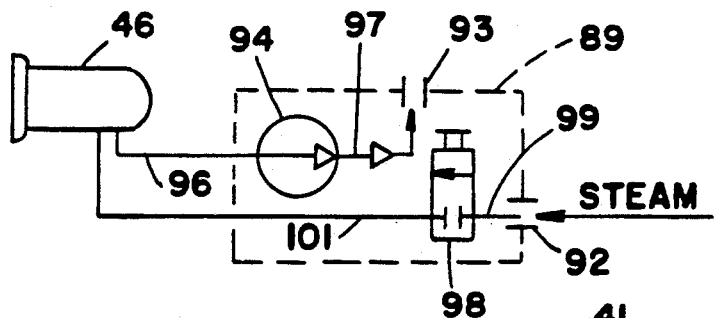
FIG_4
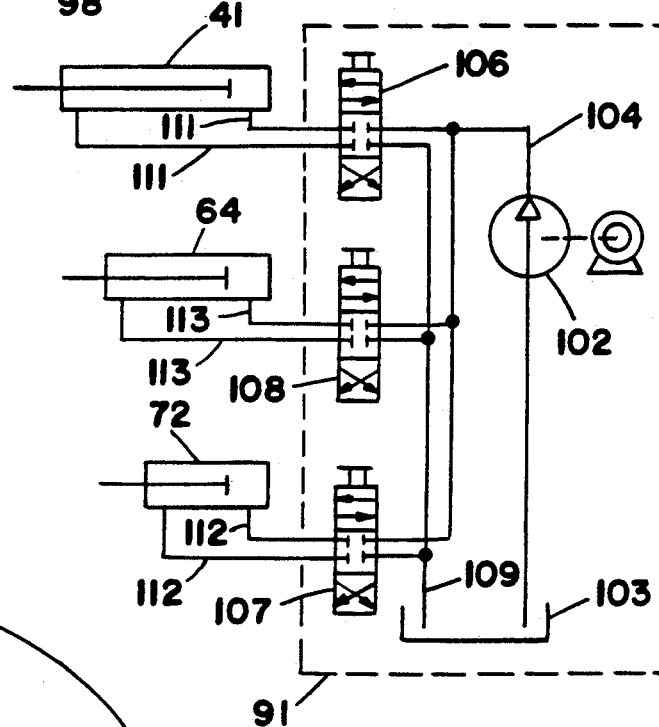
FIG_5
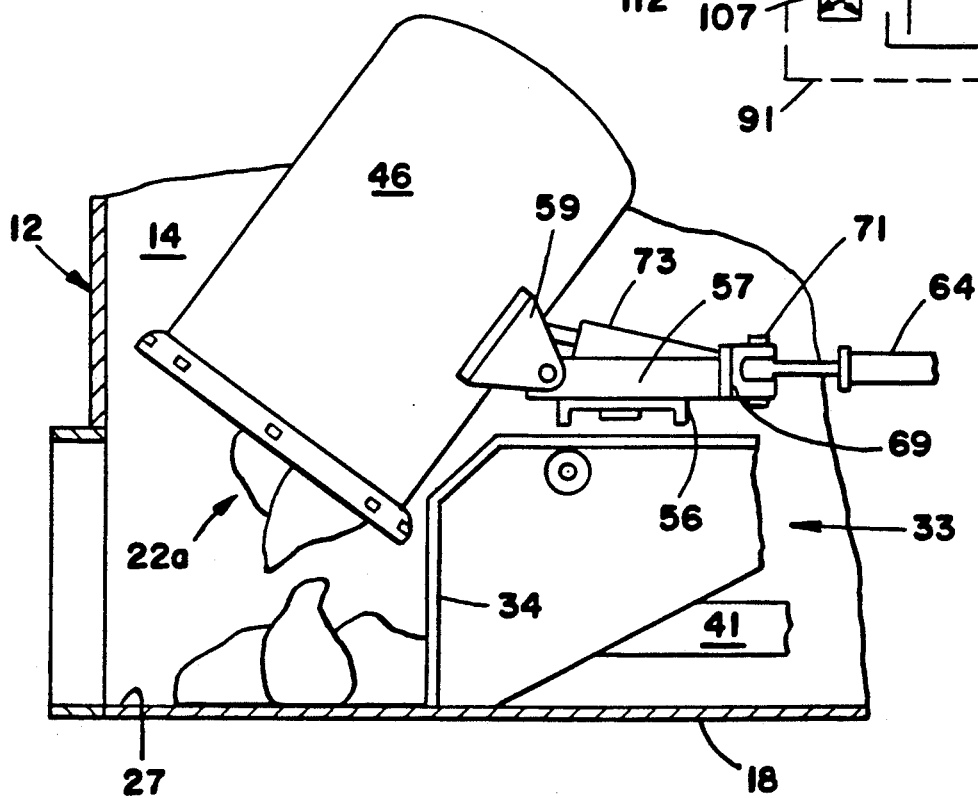
FIG_6

APPARATUS FOR TREATING AND DISPOSING OF BIO-HAZARDOUS WASTE AND SOLID WASTE

TECHNICAL FIELD

This invention relates to the processing of solid wastes and more particularly to apparatus for receiving, storing and disposing of wastes that may include infectious material.

BACKGROUND OF THE INVENTION

The handling of waste materials in hospitals, medical clinics, biological research facilities and the like requires special precautions. Various disposal items such as hypodermic needles, specimen containers or bandages and tissues, for example, may be contaminated with infectious viruses or bacteria. Waste materials of this kind should be stored in closed containers and should be sterilized prior to disposal.

Burning such wastes is not an entirely satisfactory procedure for disinfecting the material. The wastes frequently have a high moisture content and materials are often present that are not readily combustible. Consequently, incinerators for the purpose require a high fuel input and are costly to operate. Such incinerators must also be equipped with complex and costly equipment for preventing the discharge of pollutants into the atmosphere.

Sterilization of the contaminated waste by exposure to steam is simpler, more economical and less subject to complications arising from the need to suppress release of pollutants. Prior U.S. Pat. No. 4,374,491, issued Feb. 22, 1983, and entitled "Apparatus for Treating and Disposing of Bio-hazardous Waste and Solid Waste" discloses an advantageous waste processor for this purpose. The apparatus of that prior patent includes a housing having separate compartments for storing infectious and non-hazardous wastes. Contents of the infectious waste compartment are periodically sterilized by steam after which the compartment is opened and the sterilized waste is discharged into the non-hazardous waste compartment by a translatable ram. The wastes are periodically compacted and transferred to a transportable waste received by another translatable ram.

The apparatus is advantageous in that it consolidates the storage and disposal operations for both types of wastes while confining the steam heating to just that portion of the wastes that need, such treatment.

The sterilization operation can be prolonged by the presence of air in the infectious waste compartment and particularly by air trapped in the plastic bags or other containers in which the waste is usually disposed. Such air is an efficient thermal insulator and is not easily displaced by incoming steam. In some prior systems of the above described kind, the time required for sterilization of infectious waste is reduced by evacuating air from the infectious waste compartment prior to the introduction of steam.

The configuration of prior equipment of the above discussed kind requires that there be two openings in the structure which defines the infectious waste compartment. One such opening faces a side wall of the apparatus to enable wastes to be inserted into the infectious waste compartment. The other opening faces in a different direction to enable transfer of sterilized wastes from that compartment to the non-hazardous waste compartment.

Both openings require doors or other closures which preferably provide a hermetic seal to prevent the escape of steam during the sterilizing operation and to facilitate the evacuation of air from the compartment. The providing of two sealing doors or the like substantially complicates the construction of the apparatus, increases maintenance requirements and adds significantly to the cost of the apparatus.

The present invention is directed to overcoming one or more of the problems discussed above.

SUMMARY OF THE INVENTION

In one aspect of the present invention, apparatus for storing wastes prior to disposal of the waste includes a housing having at least one access opening for receiving wastes and a discharge opening through which wastes may be removed from the housing. The apparatus further includes means for receiving and storing infectious wastes at a region of the housing that is isolated from the compartment and means for sterilizing the infectious wastes at that region of the compartment. Such means includes a fluid tight receptacle having an access passage at one end for receiving and releasing waste material. The apparatus further includes receptacle support means for enabling movement of the receptacle between a first position at which the receptacle passage is in register with access opening of the housing and a second position at which the passage is tilted downward over the non-hazardous waste compartment to dump the contents of the receptacle into that compartment. A door enables selective opening and closing of the receptacle passage when the receptacle is at the first position.

In another aspect of the invention, apparatus for temporarily storing waste materials which may include bio-hazardous material has a housing with a floor, side walls, end walls and a top cover, at least one access opening in one of the side walls and a waste discharge port at the base of one of the end walls. The region of the housing which is adjacent the discharge port is a compartment for storage of non-hazardous wastes. A compactor ram is disposed in the housing for travel across the compartment and into the discharge opening. First motor means travel the compactor between an extended position at which the ram extends through the discharge opening and a retracted position at which the ram is retracted away from the discharge opening. A turntable is disposed in the housing above the retracted position of the compactor ram and is swivelable about a vertical axis. A fluid tight receptacle within the housing has a passage at one end for receiving and discharging wastes, the receptacle being pivoted to the turntable for tilting movement about a horizontal axis. Second motor means swivel the turntable and receptacle between a position at which the access passage of the receptacle faces the access opening of the housing and another position at which the access passage faces towards the end wall of the housing A sealing door is hinged to the housing at the access opening in position to close and seal the receptacle when the receptacle access passage faces the access opening of the housing. A vacuum pump enables evacuation of air from the receptacle when it is sealed by the door. The apparatus further includes means for admitting seam into the receptacle to sterilize the contents and third motor means for tilting the receptacle relative to the turntable when the access passage of the receptacle faces the end wall of the housing to dump the sterilized contents of the receptacle into the non-hazardous waste compartment.

The invention provides a waste depository in which non-hazardous and infectious wastes are initially stored at different locations and provides for periodic steam sterilization of the infectious material followed by a transfer of the sterilized waste into the non-hazardous waste compartment. Wastes are compacted and transferred from the compartment into an adjacent transportable waste receiver by actuation of a powered ram. The receptacle in which infectious wastes are initially deposited and subsequently sterilized requires only a single access passage as it is swivelable and tiltable. The receptacle access passage faces an access opening and door at the side of the housing during the period that infectious wastes are being deposited. Following sterilization of the contents, the receptacle is turned to bring the access passage over the non-hazardous waste compartment and tilted to dump the sterilized contents into that compartment. The structural and operational complications involved in providing plural openings in a hermetically sealable receptacle are avoided by utilizing a single passage for both the receipt and dumping of waste material.

The invention, including further aspects and advantages thereof, may be better understood by reference to the following description of the preferred embodiment and by reference to the accompanying drawings.

BRIEF DESCRIPTION OF THE DRAWINGS

FIG. 1 is a partially broken out side elevation view of waste storage and processing apparatus in accordance with the preferred embodiment of the invention.

FIG. 2 is a plan section view of the apparatus of FIG. 1 taken along line 2—2 thereof.

FIG. 3 is an elevation section view of a portion of the apparatus taken along line 3—3 of FIG. 2.

FIG. 4 is a schematic diagram of the vacuum and steam systems of the apparatus of the preceding figures.

FIG. 5 is a schematic diagram of fluid circuit components of the apparatus of the preceding figures.

FIG. 6 is an elevation section view of a portion of the apparatus depicting the moved position of certain components during transfer of sterilized wastes from an infectious waste receptacle to a non-hazardous waste compartment.

DETAILED DESCRIPTION OF THE PREFERRED EMBODIMENT

Referring initially to FIGS. 1 and 2 of the drawings in conjunction, apparatus 11 in accordance with this embodiment of the invention includes a housing 12 which may be of a generally rectangular configuration and which includes front and back side walls 13 and 14, respectfully, end walls 16 and 17, a floor 18 and a top cover 19. End wall 16 does not extend all the way down to floor 18 leaving an opening 21 at that end of the apparatus 11 through which stored non-hazardous wastes 22 may be transferred to an adjacent transportable waste receiver 23 of the known type in which wastes are carried to a disposal site. Such waste receivers 23 have a rectangular waste entry port 24 at the lower region of one end. The present apparatus 11 has a rectangular frame 26 which defines the waste discharge opening 21 and which protrudes a small distance from the remainder of the apparatus in order that it may enter into the entry port 24 of the waste receiver 23.

The lower region of housing 12 that is adjacent discharge opening 21 constitutes a storage compartment 27 for non-hazardous wastes 22. Such wastes 22, which are typically enclosed in plastic bags 28 or other disposable containers, are deposited in compartment 27 through an access opening 29 in the front side wall 13 situated above the compartment. Opening 29 is normally closed by a sliding door 31 which travels along horizontal tracks 32 at the outside of housing 12.

Periodically the stored wastes 22 are compacted and transfered to waste receiver 23 by actuation of a compactor ram 33. Ram 33 has an upright forward plate 34 which faces discharge opening 21 and which has a height and width similar to that of the opening. The upper region of plate 34 is inclined away from discharge opening 21 and connects with a horizontal top plate 36 of the ram that extends for a distance in the direction of housing end wall 17. Trapezoidal side plates 37 at each side of the ram 33 are welded to front plate 34 and top plate 36 to stiffen the structure. The ram 33 rides on rollers 38 which travel within channel members 39 that extend along each side of the housing 12.

Ram 33 is driven by a first linear fluid motor 41 of the known extensible and contractible rod and cylinder type. The head end 42 of motor 41 is coupled to housing end wall 17 by a pivot coupling 43 and the rod end 44 of the motor connects with forward plate 34 through another pivot coupling 45. Motor 41 is proportioned to travel ram 33 from a retracted position shown in FIG. 1 at which forward plate 34 is at the opposite side of storage compartment 27 from discharge opening 21 to an extended position at which the ram protrudes from frame 26, into waste receiver 23, for a distance of at least several inches.

Infections wastes are not deposited directly into compartment 27. Such wastes are initially placed in a fluid tight receptacle 46 which is situated above the retracted position of ram 33 and which is normally closed and sealed by a door 47. Receptacle 46 is a cylindrical drum in this example of the invention, although other configurations are also suitable, and is open at one end to provide an access passage 48 that serves both to receive and discharge wastes as will hereinafter be described in more detail.

Receptacle 46 is swivelable, by mechanism to be hereinafter described, from a first position at which the open end or access passage 48 faces the front housing side wall 13 to a second position at which the passage 48 faces housing end wall 16 which second position is depicted by dashed lines 46a in FIG. 2. Door 47 is hinged to housing 12 by arms 50 which are secured to a vertical post 49 that is rotatable relative to the housing and the door is positioned to seat in an annular dished flange 51 at the access passage 48 end of receptacle 46 when the receptacle is at the first position. The door 47 may be of any of the known forms which provide a hermetic or fluid tight seal. In the present example, the door 47 is of the type having radially directed latching arms 52 that are translatable by turning of an actuator wheel 53 and which engage in openings 54 in flange 51 with a wedging action that causes the door to exert sealing pressure against the flange. The detailed construction of such doors 47, which are extensively used to seal openings in the bulkheads of ships, are known to the art.

Referring jointly to FIGS. 2 and 3, receptacle 46 is supported in part by a fixed horizontal shelf 56 which extends between housing side walls 13 and 14 below the receptacle. A channel shaped horizontal turntable 57 is attached to shelf 56 by a pivot coupling 58 which enables swiveling of the turntable about a vertical pivot axis. A pair of support arms 59 extend down from receptacle 46 and are pivoted to the end 61 of turntable 57 by pivot couplings 62 which enable tilting of the receptacle relative to the turntable about a horizontal pivot axis. As shown in FIG. 6, the swiveling and tilting of receptacle 46 causes sterilized wastes 22a to be dumped out of the receptacle and to be deposited in the non-hazardous waste compartment 27.

Referring again to FIGS. 2 and 3 in conjunction, the swiveling movement of receptacle 46 is brought about by second motor means 63. The second motor means 63 in this example of the invention is another extensible and contractable fluid cylinder 64 having a head end 66 coupled to housing end wall 17 through a pivot coupling 67 and a rod end 68 coupled to a bracket 69 at end 61 of turntable 57 through another pivot coupling 71. Thus, with door 67 opened, contraction of the fluid cylinder 64 swings receptacle 46 to the swiveled position depicted by dashed lines 46a in FIG. 2 and extension of the cylinder reverses the movement.

Tilting of receptacle 46 from the swiveled position 46a to the downwardly inclined position depicted in FIG. 6 is brought about by third motor means 72. Referring again to FIGS. 2 and 3 in conjunction, the third motor means 72 in this example of the invention includes another extensible and contractible fluid cylinder 73 having a head end 74 coupled to turntable bracket 69 by a pivot coupling 76. Another pivot coupling 79 connects the rod end 77 to an arm 78 that extends down from receptacle 46.

Arm 78 is proportioned to locate pivot coupling 79 above the pivots 62 which couple the receptacle 46 to turntable 57. Thus extension of fluid cylinder 73 tilts the open end of receptacle 46 downward as shown in FIG. 6 and contraction of the cylinder restores the receptacle to the horizontal orientation.

Referring again to FIGS. 1 and 2, the housing access opening 29 for direct deposit of non-hazardous wastes into compartment 27 can be extended to also provide for opening of door 47 and access to receptacle 46 but, owing to the round configuration of the door and receptacle this would leave open areas in the housing. Preferably, the areas at each side of the door 47 are closed by additional housing wall members 81 and 82 which jointly define a separate, circular access opening 83 at the location of door 47. To accommodate to the swiveling movement of receptacle 46, a first portion 84 of the wall member 81 that is closest to housing end wall 17 extends inward from front side wall 13 to a location behind the flange 51 and connects with another angled portion 86 of the wall member that extends in parallel relationship with the front side wall and which forms one half of the circular access opening 83. The other wall member 82 has a first portion 87 which extends in the plane of housing front wall 13 and another portion 88 of semicircular configuration that extends inward to the location of the outer edge of receptacle flange 51.

Referring to FIG. 2 in particular, components of the steam and vacuum systems of the apparatus 11 are contained in a first sub-housing 89 situated near end wall 17 and hydraulic circuit components are within another sub-housing 91 which is also adjacent the same end wall. A first fitting 92 at end wall 17 provides for connection of sub-housing 8g with a source of pressurized steam and another fitting 93 provides for the discharge of condensed steam. Many hospitals and the like have a pre-existing supply of piped steam with which fitting 92 can be connected. In other instances a steam generator can be situated adjacent end wall 17 and be coupled to the fitting 92.

Referring to FIG. 4, components contained within the first sub-housing 89 include a vacuum pump 94 having an inlet conduit 96 which communicates with the interior of the infectious waste receptacle 46 and an outlet 97 connected to discharge fitting 93 and a steam flow control valve 98 having an inlet 99 connected to the stream intake fitting 92 and an outlet conduit 101 which also communicates with the interior of receptacle 46. Vacuum pump 94 may be of the motor driven form or may be of the aspiration type which may be operated by a flow of steam from fitting 92. Valve 98 is a two position valve having an open position at which steam is transmitted to receptacle 46 and a closed position at which the steam flow is blocked from the receptacle.

Referring to FIG. 5, hydraulic circuit components within sub-housing 91 include a pump 102 drawing fluid from a reservoir 103 and having a pressurized fluid outlet line 104 that is communicated with each of three cylinder control valves 106, 107 and 108. A drain line 109 returns fluid from each of the valves 106, 107 and 108 to reservoir 103. Valve 106 has a pair of outlet lines 111 communicated with opposite ends of the compactor ram drive cylinder 41 and has a first position at which fluid is transmitted to the head end of the cylinder and vented from the rod end of the cylinder to extend the cylinder, a second position at which the lines to both ends of the cylinder are blocked thereby immobilizing the cylinder and a third position at which fluid is transmitted to the rod end and vented from the head end to contract the cylinder.

Valve 107 is similar to valve 106 and controls the receptacle tilting fluid motor 72 in a similar manner through a pair of outlet lines 112. The third valve 108 is also similar to valve 106 and controls the receptacle swiveling fluid motor 64 through another pair of outlet lines 113.

Referring again to FIG. 1, controls 114 for the above described components of the vacuum, steam and hydraulic systems are situated at a control panel 116 on the front side wall 13 of the housing 12.

Referring to FIG. 2, the vacuum, steam and fluid lines or conduits 96, 101, 111, 112 and 113 described above are each flexible and of sufficient length to provide slack for accommodating to the previously described movements of the receptacle 46 and fluid motors 41, 64 and 72. With reference to FIG. 3, a manifold plate 117 having an array of small apertures. 118 extends across the bottom region of receptacle 46. Vacuum line 96 communicates with the receptacle 46 through a fitting 119 situated below plate 117 at the lowest portion of the receptacle. Steam supply line 101 communicates with the receptacle 46 through another fitting 121 which is also situated below plate 117. The manifold plate 117 holds the stored wastes above any condensed steam or other liquid that may accumulate at the bottom of receptacle 46, assures a dispersed distribution of steam into the receptacle and prevents blockage of the steam inlet and vacuum inlet by wastes contained in the receptacle.

In operation, non-hazardous wastes 22 are directly deposited in compartment 27 by temporarily opening the sliding door 31. Infectious wastes 22a are placed in receptacle 46 by temporarily opening sealing door 47 which is preferably lockable to prevent unauthorized access. Periodically, the compactor ram 33 is actuated to compress non-hazardous wastes 22 which have been accumulated in compartment 27 and to transfer such wastes into receiver 23. Material which has accumulated in receptacle 46 is then sterilized. Sterilization is accomplished by temporarily actuating vacuum pump 94 to exhaust air from the receptacle 46 including from the interior of waste containers 22a that are present in the receptacle. Valve 98 is then opened to admit hot pressurized steam into the receptacle 46. Steam exposure times of about one half hour or more may be needed to assure sterilization of the infectious wastes. Operation of vacuum pump 94 may be continued at a reduced rate during the steam sterilization period to establish a continuous flow of steam through the receptacle 46 and to withdraw any condensed steam that accumulates at the bottom of the receptacle.

Following the sterilization period, the steam flow control valve 98 is closed, sealing door 47 is opened and receptacle 46 is swiveled by operating motor control valve 108 The receptacle 46 is then tilted by operation of motor control valve 107 to dump the sterilized wastes into compartment 27 after which the receptacle is brought back to the original orientation by operation of such valves. Compactor ram 33 is again advanced and retracted to transfer the sterilized wastes into receiver 23. The apparatus 11 may then be used to receive, store and process additional waste materials.

While the invention has been disclosed with respect to a single preferred embodiment, many modifications and variations of the structure are possible and it is not intended to limit the invention except as defined by the following claims.

I claim:

1. In apparatus for storing wastes prior to disposal thereof, said apparatus having a housing with a compartment for receiving and storing non-hazardous wastes, at least one access opening for receiving wastes and a discharge opening through which wastes may be removed from said housing for disposal, said apparatus further including means for receiving and storing infectious wastes at a region of said housing that is isolated from said compartment and means for sterilizing said infectious wastes at said region of said housing, the improvement comprising:

said means for receiving and storing infectious waste material comprising a fluid tight receptacle having an access passage at one end for receiving and releasing waste material, said apparatus further including receptacle support means for enabling movement of said receptable between a first position at which said receptacle passage is in register with said at least one access opening of said housing and a second position at which said passage is tilted downward over said compartment to dump contents of said receptacle into said compartment, and a door positioned and arranged for selectively opening and closing said receptacle passage when said receptacle is at said first position thereof.

2. The apparatus of claim 1 wherein said housing has a side wall at which said at least one access opening is located and an end wall at which said discharge opening is located, wherein said receptacle extends transversely within said housing when said receptacle is at said first position thereof, and wherein said receptable support means is constructed and arranged so as to enable swiveling movement of said receptacle about a vertical axis and tilting movement of said receptable about a horizontal axis to bring said receptacle to said second position thereof.

3. The apparatus of claim 2 further including motor means for turning said receptacle about said horizontal and vertical axes.

4. The apparatus of claim 1 further including a movable waste compaction ram disposed in said housing and being movable between a retracted position at which said ram is spaced from said discharge opening of said housing and is below said receptacle and an extended position at which said ram extends out of said housing through said discharge opening, and wherein said receptacle passage is positioned over the region between said ram and said discharge opening of said housing when said receptacle is at said second position thereof and said ram is at said retracted position thereof.

5. The apparatus of claim 1 wherein said door is pivoted to said housing at said at least one access opening thereof in position to close said access passage of said receptacle when said receptacle is at said first position thereof.

6. The apparatus of claim 1 wherein said means for sterilizing said infectious wastes includes a steam flow control valve for connection to a source of steam and a flexible steam conduit connected between said valve and said receptacle, said flexible steam conduit having a length greater than the spacing of said receptacle from said valve when said receptacle is at said first position thereof.

7. The apparatus of claim 6 further including a manifold plate having a plurality of spaced apart apertures therein, said plate being secured within said receptable and positioned to separate a lower region of the interior of said receptacle from an upper region of the interior of said receptacle, and wherein said flexible steam conduit is in communication with said lower region.

8. The apparatus of claim 6 further including a vacuum pump and another flexible conduit connecting said vacuum pump with the interior of said receptacle.

9. The apparatus of claim 1 wherein said receptacle support means includes a fixed horizontal shelf within said housing, a horizontal turntable coupled to said shelf and being swivelable about a vertical axis and at least one support arm extending downward from said receptacle to said turntable and being pivotably coupled to said turntable for pivoting movement about a horizontal axis.

10. The apparatus of claim 9 further including a compactor ram disposed in said housing for travel across a lower region of said compartment and into said discharge opening of said housing, a first fluid motor coupled to said compactor ram and being oriented to travel said compactor ram towards said discharge opening and away therefrom, a second fluid motor coupled to said turntable to swivel said turntable about said vertical axis and a third fluid motor coupled to said shelf and said receptacle to tilt said receptacle about said horizontal axis.

11. Apparatus for temporarily storing waste materials which may include bio-hazardous waste materials comprising:

a housing having a floor, side walls, end walls and a top cover, said housing having at least one access opening in one of said sidewalls and having a waste discharge port at the base of one of said end walls, the region of said housing which is adjacent said discharge port being a compartment for storage of non-hazardous wastes,
a compactor ram disposed in said housing for travel across said compartment and into said discharge opening,
first motor means for traveling said compactor ram between an extended position at which said compactor ram extends through said discharge opening and a retracted position at which said ram is retracted away from said discharge opening,
a turntable disposed in said housing above said retracted position of said compactor ram and being swivelable about a vertical axis,
a fluid tight receptacle disposed in said housing and having an access passage at one end for receiving and discharging bio-hazardous wastes, said receptacle being pivoted to said turntable for tilting movement about a horizontal axis,
second motor means for swiveling said turntable and receptacle between a position at which said access passage of said receptacle faces said at least one access opening of said housing and another position at which said access passage faces towards said one of said end walls of said housing,
a sealing door hinged to said housing at said at least one access opening in position to close and seal said receptacle when said access passage thereof faces said at least one access opening of said housing,
a vacuum pump communicated with said receptacle for evacuating air therefrom when said receptacle is sealed by said door,
means for admitting steam into said evacuated receptacle to sterilize the contents thereof, and
third motor means for tilting said receptacle relative to said turntable when said access passage faces said one of said end walls of said housing to dump the contents of said receptacle into said non-hazardous waste compartment.

12. The apparatus of claim 11 wherein said first, second and third motor means are extensible and contractible fluid motors of the rod and cylinder type.

* * * * *